US011113023B2

(12) United States Patent
Rando et al.

(10) Patent No.: US 11,113,023 B2
(45) Date of Patent: Sep. 7, 2021

(54) MEDIA CONTENT SYSTEM FOR ENHANCING REST

(71) Applicant: Spotify AB, Stockholm (SE)

(72) Inventors: Mateo Rando, Stockholm (SE); Tristan Jehan, Brooklyn, NY (US)

(73) Assignee: Spotify AB, Stockholm (SE)

( * ) Notice: Subject to any disclaimer, the term of this patent is extended or adjusted under 35 U.S.C. 154(b) by 0 days.

(21) Appl. No.: 16/503,327

(22) Filed: Jul. 3, 2019

(65) Prior Publication Data

US 2020/0019371 A1    Jan. 16, 2020

Related U.S. Application Data

(63) Continuation of application No. 15/090,184, filed on Apr. 4, 2016, now Pat. No. 10,387,106.

(51) Int. Cl.
*G10H 1/40* (2006.01)
*G06F 3/16* (2006.01)
(Continued)

(52) U.S. Cl.
CPC .............. *G06F 3/165* (2013.01); *A61B 5/024* (2013.01); *A61B 5/02416* (2013.01); *A61B 5/486* (2013.01); *A61M 21/02* (2013.01); *H04N 21/42201* (2013.01); *A61B 5/6898* (2013.01); *A61M 2021/0027* (2013.01);
(Continued)

(58) Field of Classification Search
CPC ........... G06F 3/165; A61B 5/024; G10H 1/40; G10H 2220/371; G10H 2240/131; G10H 1/0025; G10H 2210/076; G10H 2210/391; G10H 2250/035; G10H 2220/081; G10H 2220/376; G10H 2210/375;
(Continued)

(56) References Cited

U.S. PATENT DOCUMENTS 5,577,990 A    11/1996 Widjaja et al.
7,521,623 B2 *    4/2009 Bowen .................... G06F 16/22
                                                 84/612

(Continued)

FOREIGN PATENT DOCUMENTS

WO    2008/009978 A1    1/2008
WO    2010/058065 A1    5/2010

OTHER PUBLICATIONS

Kurt Kräuchi and Anna Wirz-Juztice, Ph.D.: "Circadian Clues to Sleep Onset Mechanisms", Neuropsychopharmacology, Recent Advances in Sleep and Chronobiology, vol. 25, Issue 5, Supplement 1, Nov. 2001, pp. S92-S96.

(Continued)

*Primary Examiner* — Marlon T Fletcher
(74) *Attorney, Agent, or Firm* — Merchant & Gould P.C.

(57) ABSTRACT

A media-playback device acquires a heart rate, selects a song with a first tempo, and initiates playback of the song. The song meets a set of qualification criteria and the first tempo is based on the heart rate, such as being equal to or less than the heart rate. The media-playback device also initiates playback of a binaural beat at a first frequency. Over a period of time, the binaural beat's first frequency is changed to a second frequency. Over the period of time, the first tempo can also be changed to a second tempo, where the second tempo is slower than the first tempo.

19 Claims, 12 Drawing Sheets

(51) Int. Cl.
*A61B 5/024* (2006.01)
*A61M 21/02* (2006.01)
*A61B 5/00* (2006.01)
*H04N 21/422* (2011.01)
*A61M 21/00* (2006.01)

(52) U.S. Cl.
CPC .............. *A61M 2021/0061* (2013.01); *A61M 2205/3553* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/584* (2013.01); *A61M 2230/06* (2013.01); *G10H 2210/021* (2013.01); *G10H 2210/076* (2013.01)

(58) Field of Classification Search
CPC ....... G10H 2240/135; G10H 2240/145; G10H 2240/141; A61H 2230/04; G10G 1/00
USPC .......................................................... 707/722
See application file for complete search history.

(56) References Cited

U.S. PATENT DOCUMENTS

| | | | |
|---|---|---|---|
| 7,705,230 B2 * | 4/2010 | Bowen | G10H 1/18 84/612 |
| 7,973,231 B2 * | 7/2011 | Bowen | G06F 3/015 84/612 |
| 8,704,068 B2 * | 4/2014 | Bowen | A63B 71/0686 84/612 |
| 8,932,218 B1 | 1/2015 | Thompson | |
| 9,230,527 B2 * | 1/2016 | Bowen | G06F 3/165 |
| 9,563,268 B2 | 2/2017 | Smith et al. | |
| 9,570,059 B2 | 2/2017 | Garmark et al. | |
| 10,029,066 B2 * | 7/2018 | Park | A61B 5/4836 |
| 10,152,957 B2 * | 12/2018 | Lenhert | G10H 1/0025 |
| 10,387,106 B2 * | 8/2019 | Rando | G06F 3/165 |
| 2006/0136009 A1 * | 6/2006 | Staffel | A61N 1/36025 607/46 |
| 2006/0252978 A1 * | 11/2006 | Vesely | A61B 5/0482 600/27 |
| 2006/0252979 A1 * | 11/2006 | Vesely | A61B 5/6803 600/27 |
| 2007/0131097 A1 * | 6/2007 | Lu | A63B 69/0028 84/615 |
| 2007/0203421 A1 | 8/2007 | Cho et al. | |
| 2008/0269652 A1 * | 10/2008 | Reiner | 601/15 |
| 2010/0010289 A1 * | 1/2010 | Clare | A61B 5/16 600/27 |
| 2010/0191037 A1 * | 7/2010 | Cohen | A61M 21/00 600/28 |
| 2011/0066041 A1 * | 3/2011 | Pandia | A61B 5/029 600/484 |
| 2011/0113330 A1 * | 5/2011 | Olsson | G06F 16/639 715/716 |
| 2014/0074479 A1 * | 3/2014 | Kassam | G10L 25/48 704/270 |
| 2014/0281971 A1 * | 9/2014 | Isbell, III | H04N 21/42202 715/716 |
| 2014/0350706 A1 * | 11/2014 | Morishima | A61B 5/4815 700/94 |
| 2014/0358012 A1 | 12/2014 | Richards et al. | |
| 2015/0092972 A1 * | 4/2015 | Lai | H04R 1/1008 381/333 |
| 2015/0251053 A1 * | 9/2015 | Hoffman | G16H 40/67 700/91 |
| 2015/0258383 A1 * | 9/2015 | Quatrochi | A61B 5/6807 700/91 |
| 2015/0320328 A1 * | 11/2015 | Albert | A61B 5/02125 600/480 |
| 2015/0375106 A1 * | 12/2015 | Liu | A63F 13/211 463/31 |
| 2016/0008568 A1 * | 1/2016 | Attia | A61B 5/486 600/28 |
| 2016/0029946 A1 * | 2/2016 | Simon | A61B 5/048 600/544 |
| 2016/0210952 A1 * | 7/2016 | Turner | G10H 7/00 |
| 2016/0342687 A1 | 11/2016 | Garmark et al. | |
| 2016/0343363 A1 * | 11/2016 | Garmark | G06F 3/165 |
| 2017/0039045 A1 * | 2/2017 | Abrahami | A61B 5/1118 |
| 2017/0061760 A1 * | 3/2017 | Lee | A61B 5/02427 |
| 2017/0094385 A1 * | 3/2017 | Lee | A61M 21/00 |
| 2017/0149945 A1 * | 5/2017 | Lee | G06F 3/165 |
| 2017/0173296 A1 * | 6/2017 | Park | A61B 5/024 |
| 2017/0286536 A1 * | 10/2017 | Rando | G06F 3/165 |
| 2017/0287325 A1 * | 10/2017 | Filatova | G08C 23/04 |
| 2017/0300567 A1 | 10/2017 | Jehan et al. | |
| 2017/0301372 A1 | 10/2017 | Jehan et al. | |
| 2017/0345273 A1 * | 11/2017 | Lee | G08B 3/1025 |
| 2018/0070887 A1 * | 3/2018 | Lee | A61B 5/0004 |
| 2018/0084095 A1 * | 3/2018 | Lee | G06F 3/167 |
| 2018/0085009 A1 * | 3/2018 | Aiello | A61B 5/7278 |
| 2018/0110960 A1 * | 4/2018 | Youngblood | A61B 5/0031 |
| 2018/0133431 A1 * | 5/2018 | Malchano | A61B 5/0036 |
| 2018/0133504 A1 * | 5/2018 | Malchano | A61N 1/36025 |
| 2018/0133507 A1 * | 5/2018 | Malchano | A61M 21/00 |
| 2018/0166053 A1 * | 6/2018 | Turner | G10H 1/40 |
| 2018/0240027 A1 * | 8/2018 | Karanam | G06F 19/3481 |
| 2018/0261332 A1 * | 9/2018 | Baeuerle | G16H 50/50 |
| 2018/0317784 A1 * | 11/2018 | Albert | A61B 5/404 |
| 2018/0344968 A1 * | 12/2018 | Gordon | G06N 20/00 |
| 2019/0080592 A1 * | 3/2019 | Filatova | G08C 23/04 |
| 2020/0019371 A1 * | 1/2020 | Rando | A61B 5/02416 |
| 2020/0258489 A1 * | 8/2020 | Turner | G10H 7/00 |

OTHER PUBLICATIONS

Vera Abeln et al.: "Brainwave entrainment for better sleep and post-sleep state of young elite soccer players—A pilot study", European Journal of Sport Science, vol. 14, No. 5, 2014, pp. 393-402.

International Search Report and Written Opinion from International Application No. PCT/IB2017/000449 (dated Jul. 14, 2017).

International Preliminary Report on Patentability from International Application No. PCT/IB2017/000449 (dated Oct. 9, 2018).

* cited by examiner

MEDIA CONTENT SYSTEM FOR ENHANCING REST

CROSS-REFERENCE TO RELATED APPLICATION(S)

This application is a Continuation of U.S. patent application Ser. No. 15/090,184, filed on Apr. 4, 2016, titled MEDIA CONTENT SYSTEM FOR ENHANCING REST, the disclosure of which is hereby incorporated by reference in its entirety.

BACKGROUND

Some people enjoy listening to music to relax or before sleeping. Common musical genres used to induce relaxation include classical, jazz, and reggae. Other people may enjoy listening to relaxation-focused musical genres, such as downtempo electronic or new age.

SUMMARY

In general terms, this disclosure is directed to a media content system. In some embodiments, and by non-limiting example, the media content system is for enhancing rest.

One aspect is a computing device, where the computing device includes at least one processing device and at least one computer readable data storage device storing instructions. The instructions, when executed by the at least one processing device, cause a media-playback device to: acquire a heart rate, select at least one media content item with a first tempo, where the at least one media content item meets a set of qualification criteria and where the first tempo is based on the heart rate. The instructions also cause the media-playback device to initiate playback of the at least one media content item. Over a period of time during the playback of the at least one media content item, the first tempo is changed to a second tempo, the second tempo being slower than the first tempo. The instructions also cause the media-playback device to initiate playback of a binaural beat at a first frequency during the playback of the at least one media content item and, over the period of time during the playback of the at least one media content item, change the binaural beat to a second frequency.

Another aspect is a method for selecting and playing a song. The method includes, using a computing device: acquiring a heart rate, acquiring a moment selection, selecting at least one song with a first tempo, where the at least one song meets a set of qualification criteria and where the first tempo is based on the heart rate and the moment selection. The method also includes, using the computing device: initiating playback of the at least one song, initiating playback of a binaural beat at a first frequency at least partially during the playback of the at least one song, and causing the binaural beat to change to a second frequency during the playback of the at least one song.

A further aspect is a media server. The media server includes a database, at least one processing device in data communication with the database, and at least one computer readable storage device storing data instructions. The database stores at least a plurality of songs that meet a set of qualification criteria, the set of qualification criteria including: a major key and an absence of lyrics. The instructions, when executed by the at least one processing device, cause the media server to: acquire a heart rate, select a song from the plurality of songs, where the song has a first tempo and wherein the first tempo is based on the heart rate, initiate playback of the song, initiate playback of a binaural beat at a first frequency during the playback of the song, and over a period of time during the playback of the song, change the binaural beat to a second frequency.

DETAILED DESCRIPTION

Figure 1:
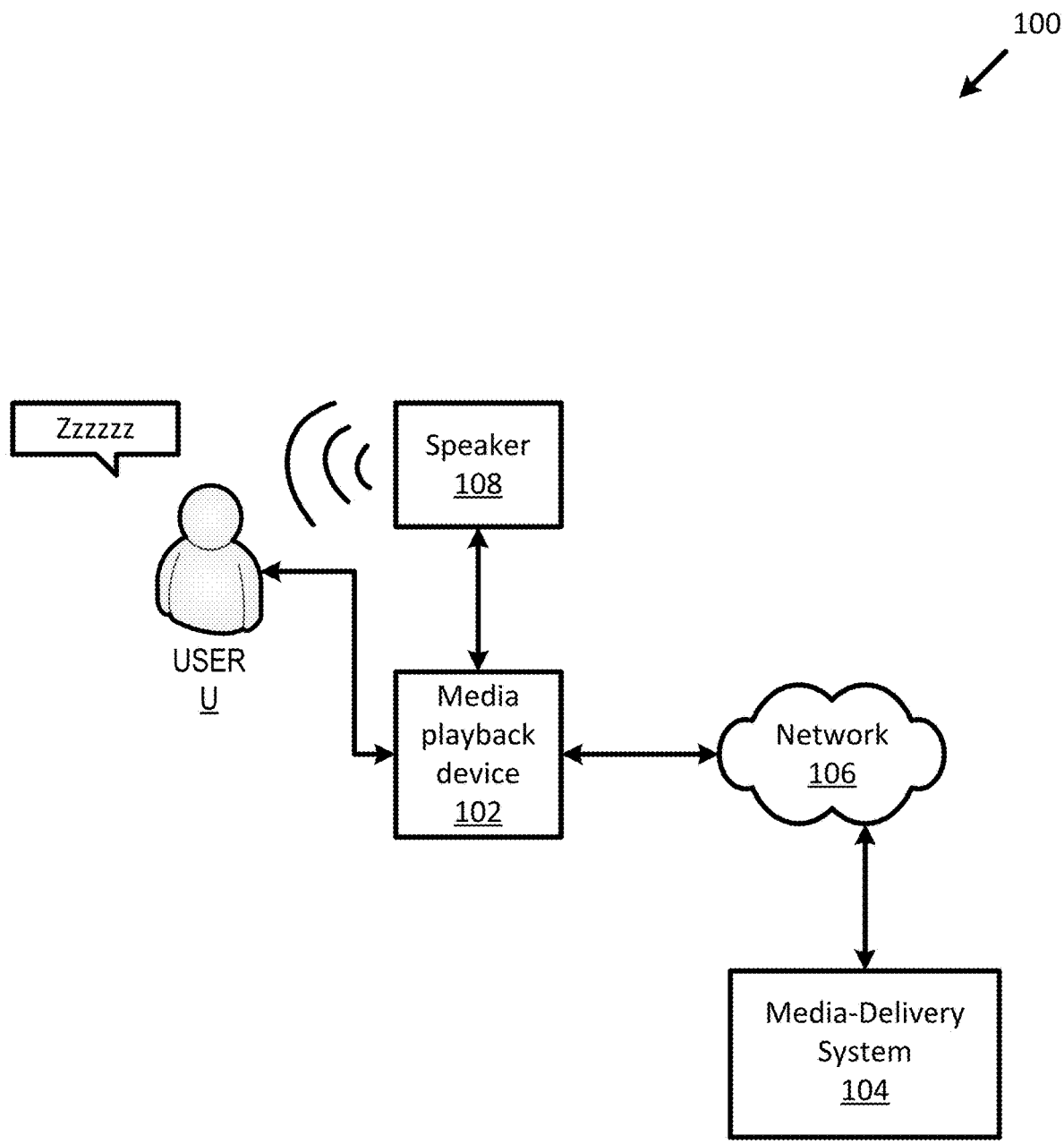
FIG. 1 illustrates an example system for restful media content selection.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Users of media-playback devices often consume media content while engaging in various activities, including while resting. For example, users may choose to unwind after work or have a massage while listening to relaxing music. Additionally, as an example, users may choose to listen to music before or during a nap or their nighttime rest. Consuming media content may include one or more of listening to audio content, watching video content, or consuming other types of media content. For ease of explanation, the embodiments described in this application are presented using specific examples. For example, audio content (and in particular music) is described as an example of one form of media content. As another example, nighttime sleeping is described as an example of one form of rest. However, it should be understood that the same concepts are equally applicable to other forms of media consumption and to other forms of rest, and at least some embodiments include other forms of media consumption and/or other forms of rest.

FIG. 1 illustrates an example system 100 for restful media content selection. The example system 100 includes a media-playback device 102, a media-delivery system 104, and a speaker 108. The system 100 communicates across a network 106. Also shown is a user U who desires to listen to relaxing or sleep-related music. Other embodiments can include more or fewer components.

The media-playback device 102 operates to play media content items 105 to produce media output 110. In some embodiments, the media content items 105 are provided by the media-delivery system 104 and transmitted to the media-playback device using the network 106. A media content item 105 is an item of media content, including audio, video, or other types of media content, which may be stored in any format suitable for storing media content. Non-limiting examples of media content items 105 include songs, albums, music videos, movies, television episodes, podcasts, other types of audio or video content, and portions or combinations thereof.

In some embodiments, the media-playback device 102 plays media content for the user U based on the user's input and heart rate. The media-playback device 102 can acquire the user's U heart rate via, for example, user input, peripheral device, or its own hardware and software. The tempo (or rhythm) of music refers to the frequency of the beat and is typically measured in beats per minute (bpm). The beat is the basic unit of rhythm in a musical composition (as determined by the time signature of the music). Accordingly, in the example shown, the user's U heart rate is related to the tempo of the music. Selecting one or more tempos is discussed in more detail with reference to FIGS. 3-6, below.

Speaker 108 generates audible sounds to audibly reproduce the media content item 105 received from the media-playback device 102 as media output 110. In some embodiments, speaker 108 is integral with media-playback device 102. In other embodiments, speaker 108 is a separate component from the media-playback device 102. In embodiments, media-playback device 102 and speaker 108 communicate wirelessly. For example, speaker 108 is a portable stereo, a clock radio, a stereo receiver, headphones, or a stand-alone speaker. Additionally, speaker 108 can be a device compatible with Spotify Connect™, Bluetooth™, Apple™ AirPlay™, and Google™ Cast™.

Figure 2:
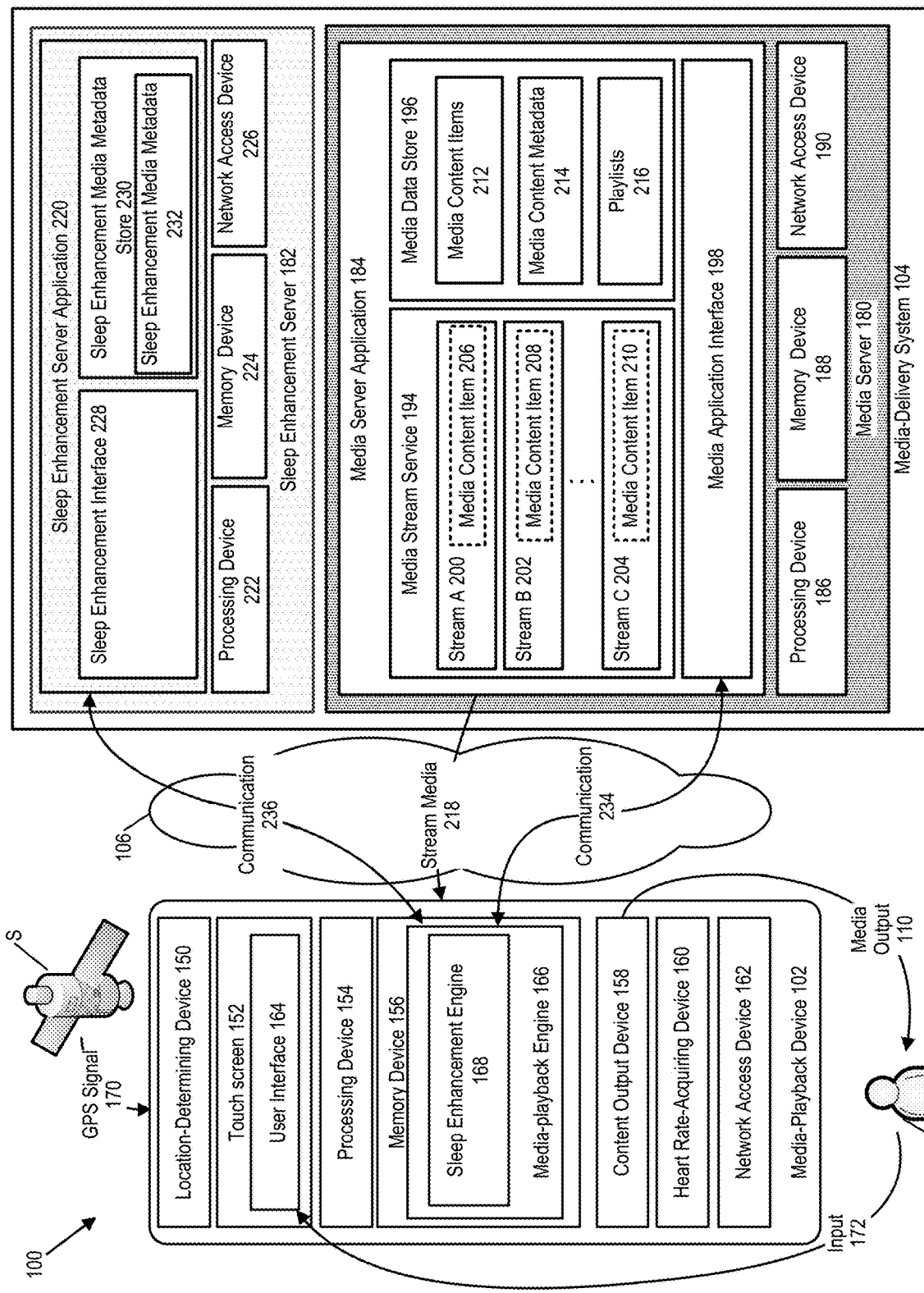
FIG. 2 illustrates a schematic diagram of an example system for heart rate determination and media content selection.

FIG. 2 is a schematic illustration of another example of the system 100 for restful media content selection shown in FIG. 1. In FIG. 2, the media-playback device 102, the media-delivery system 104, and the network 106 are shown. Also shown are the user U and a satellite S.

As noted above, the media-playback device 102 operates to play media content items 105. In some embodiments, the media-playback device 102 operates to play media content items 105 that are provided (e.g., streamed, transmitted, etc.) by a system external to the media-playback device such as the media-delivery system 104, another system, or a peer device. Alternatively, in some embodiments, the media-playback device 102 operates to play media content items 105 stored locally on the media-playback device 102. Further, in at least some embodiments, the media-playback device 102 operates to play media content items 105 that are stored locally as well as media content items 105 provided by other systems.

In some embodiments, the media-playback device 102 is a computing device, handheld entertainment device, smartphone, tablet, watch, wearable device, or any other type of device capable of playing media content. In some embodiments, the media-playback device 102 is a laptop computer, desktop computer, television, gaming console, set-top box, network appliance, blue-ray or DVD player, media player, stereo, or radio. Commercially-available examples include the Apple™ iPod™, Apple™ iPad™, Apple™ iPhone, Apple™ TV™, a Roku™ device such as Roku™ 3, Sony™ Playstation 4™, and Microsoft™ Xbox™.

In at least some embodiments, the media-playback device 102 includes a location-determining device 150, a touch screen 152, a processing device 154, a memory device 156, a content output device 158, a heart rate-acquiring device 160, and a network access device 162. Other embodiments of the media-playback device 102 may include additional, different, or fewer components than the example shown in FIG. 2. For example, some embodiments may include a recording device such as a microphone or camera that operates to record audio or video content. As another example, some embodiments do not include one or more of the location-determining device 150 and the touch screen 152.

The location-determining device 150 is a device that determines the location of the media-playback device 102. In some embodiments, the location-determining device 150 uses one or more of the following technologies: Global Positioning System (GPS) technology which may receive GPS signals 170 from satellites S, cellular triangulation technology, network-based location identification technology, Wi-Fi positioning systems technology, and combinations thereof.

The touch screen 152 operates to receive an input 172 from a selector (e.g., a finger, stylus etc.) controlled by the user U. In some embodiments, the touch screen 152 operates as both a display device and a user input device. In some embodiments, the touch screen 152 detects inputs based on one or both of touches and near-touches. In some embodiments, the touch screen 152 displays a user interface 164 for interacting with the media-playback device 102. As noted above, some embodiments do not include a touch screen 152. Some embodiments include a display device and one or more separate user interface devices. Further, some embodiments do not include a display device.

In some embodiments, the processing device 154 comprises one or more central processing units (CPU). In other embodiments, the processing device 154 additionally or alternatively includes one or more digital signal processors, field-programmable gate arrays, or other electronic circuits.

The memory device 156 operates to store data and instructions. In some embodiments, the memory device 156 stores instructions for a media-playback engine 166 that includes a rest enhancement engine 168. In some embodiments, the media-playback engine 166 operates to playback media content and the rest enhancement engine 168 operates to select media content for playback based on a heart rate.

The memory device 156 typically includes at least some form of computer-readable media. Computer readable media includes any available media that can be accessed by the media-playback device 102. By way of example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media includes, but is not limited to, random access memory, read only memory, electrically erasable programmable read only memory, flash memory and other memory technology, compact disc read only memory, blue ray discs, digital versatile discs or other optical storage, magnetic cassettes, magnetic tape, magnetic disk storage or other magnetic storage devices, or any other medium that can be used to store the desired information and that can be accessed by the media-playback device 102. In some embodiments, computer readable storage media is non-transitory computer readable storage media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The content output device 158 operates to output media content. In some embodiments, the content output device 158 generates media output 110 for the user U. Examples of the content output device 158 include a speaker 108, an audio output jack, a Bluetooth transmitter, a display panel, and a video output jack. Other embodiments are possible as well. For example, the content output device 158 may transmit a signal through the audio output jack or Bluetooth transmitter that can be used to reproduce an audio signal by a connected or paired device such as headphones or a speaker.

The heart rate-acquiring device 160 operates to acquire a heart rate associated with the user U. In at least some embodiments, the heart rate-acquiring device 160 operates to determine heart rate directly. One example of the heart rate-acquiring device 160 (illustrated and described in more detail with reference to FIGS. 9A and 9B) detects the user's U heart rate by having the user U position a finger over a camera lens on the media-playback device 102. Then, an application stored on media-playback device 102 analyzes the images received to determine the pulse rate (heart rate) of user U. In some embodiments, the application detects changes in color and associates the rate of change in color to the movement of blood through the finger, which is related to the user's U pulse rate. Additionally, some media-playback devices 102 currently available include a heart rate monitor, such as the Samsung Galaxy S5.

Alternatively, the heart rate-acquiring device 160 operates to receive data representing a heart rate associated with the user U. For example, in some embodiments, the heart rate-acquiring device 160 operates to receive data from a watch, wrist band, chest strap, or other device for determining or measuring heart rate. Further, in some embodiments, the heart rate-acquiring device 160 operates to receive a heart rate value input by the user U or another person.

The network access device 162 operates to communicate with other computing devices over one or more networks, such as the network 106. Examples of the network access device include wired network interfaces and wireless network interfaces. Wireless network interfaces includes infrared, BLUETOOTH® wireless technology, 802.11a/b/g/n/ac, and cellular or other radio frequency interfaces in at least some possible embodiments.

The network 106 is an electronic communication network that facilitates communication between the media-playback device 102 and the media-delivery system 104. An electronic communication network includes a set of computing devices and links between the computing devices. The computing devices in the network 106 use the links to enable communication among the computing devices in the network 106. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links, including Bluetooth, ultra-wideband (UWB), 802.11, ZigBee, cellular, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Further, in some embodiments, the network 106 includes multiple networks, which may be of the same type or of multiple different types.

The media-delivery system 104 comprises one or more computing devices and operates to provide media content items 105 to the media-playback devices 102 and, in some embodiments, other media-playback devices as well. In some embodiments, the media-delivery system 104 includes a media server 180 and a rest enhancement server 182. In at least some embodiments, the media server 180 and the rest enhancement server 182 are provided by separate computing devices. In other embodiments, the media server 180 and the rest enhancement server 182 are provided by the same one or more computing devices. Further, in some embodiments, one or both of the media servers 180 and the rest enhancement server 182 are provided by multiple computing devices. For example, the media server 180 and the rest enhancement server 182 may be provided by multiple redundant servers located in multiple geographic locations.

The media server 180 operates to transmit stream media 218 to media-playback devices such as the media-playback device 102. In some embodiments, the media server 180 includes a media server application 184, a processing device 186, a memory device 188, and a network access device 190. The processing device 186, memory device 188, and network access device 190 may be similar to the processing device 154, memory device 156, and network access device 162 respectively, which have each been previously described.

In some embodiments, the media server application 184 operates to stream music or other audio, video, or other forms of media content. The media server application 184 includes a media stream service 194, a media data store 196, and a media application interface 198. The media stream service 194 operates to buffer media content such as media content 206, 208, and 210, for streaming to one or more streams 200, 202, and 204.

The media application interface 198 can receive requests or other communication from media-playback devices or other systems, to retrieve media content items 105 from the media server 180. For example, in FIG. 2, the media application interface 198 receives communication 234 from the media-playback engine 166.

In some embodiments, the media data store 196 stores media content items 210, media content metadata 212, and playlists 214. The media data store 196 may comprise one or more databases and file systems. Other embodiments are possible as well. As noted above, the media content items 210 may be audio, video, or any other type of media content, which may be stored in any format for storing media content.

The media content metadata 212 operates to provide various information associated with the media content items 210. In some embodiments, the media content metadata 212 includes one or more of title, artist name, album name, length, genre, mood, era, etc. The playlists 214 operate to identify one or more of the media content items 210. In some embodiments, the playlists 214 identify a group of the media content items 210 in a particular order. In other embodiments, the playlists 214 merely identify a group of the media content items 210 without specifying a particular order. Some, but not necessarily all, of the media content items 210 included in a playlist 214 are associated with a common characteristic such as a common genre, mood, or era.

The rest enhancement server 182 operates to provide rest enhancement-specific information about media content items to media-playback devices. In some embodiments, the rest enhancement server 182 includes a rest enhancement server application 220, a processing device 222, a memory device 224, and a network access device 226. The processing device 222, memory device 224, and network access device 226 may be similar to the processing device 154, memory device 156, and network access device 162 respectively, which have each been previously described.

In some embodiments, rest enhancement server application 220 operates to transmit information about the suitability of one or more media content items for playback during a particular rest enhancement. The rest enhancement server application 220 includes a rest enhancement interface 228 and a rest enhancement media metadata store 230.

In some embodiments, the rest enhancement server application 220 provides a list of media content items at a particular tempo to a media-playback device in response to a request that includes a particular heart rate value. Further, in some embodiments, the media content items included in the returned list are particularly relevant for the mood and rest enhancement in which the user is engaged (for example, if the user is taking a power nap, the returned list of media content items may include only media content items that have been identified as being useful for power naps).

The rest enhancement interface 228 operates to receive requests or other communication from media-playback devices or other systems, to retrieve information about media content items from the rest enhancement server 182. For example, in FIG. 2, the rest enhancement interface 228 receives communication 234 from the media-playback engine 166.

In some embodiments, the rest enhancement media metadata store 230 stores rest enhancement media metadata 232. The rest enhancement media metadata store 230 may comprise one or more databases and file systems. Other embodiments are possible as well.

The rest enhancement media metadata 232 operates to provide various information associated with media content items, such as the media content items 210. In some embodiments, the rest enhancement media metadata 232 provides information that may be useful for selecting media content items for playback during a rest enhancement. For example, in some embodiments, the rest enhancement media metadata 232 stores restability scores for media content items that correspond to the suitability of particular media content items for playback during resting or relaxation. As another example, in some embodiments, the rest enhancement media metadata 232 stores timestamps (e.g., start and end points) that identify portions of media content items that are particularly well-suited for playback during rest enhancement.

Each of the media-playback device 102 and the media-delivery system 104 can include additional physical computer or hardware resources. In at least some embodiments, the media-playback device 102 communicates with the media-delivery system 104 via the network 106.

Although in FIG. 2 only a single media-playback device 102 and media-delivery system 104 are shown, in accordance with some embodiments, the media-delivery system 104 can support the simultaneous use of multiple media-playback devices, and the media-playback device can simultaneously access media content from multiple media-delivery systems. Additionally, although FIG. 2 illustrates a streaming media based system for heart rate determination and media content selection, other embodiments are possible as well. For example, in some embodiments, the media-playback device 102 includes a media data store 196 and the media-playback device 102 is configured to perform heart rate determination and media content selection without accessing the media-delivery system 104. Further in some embodiments, the media-playback device 102 operates to store previously streamed media content items in a local media data store.

In at least some embodiments, the media-delivery system 104 can be used to stream, progressively download, or otherwise communicate music, other audio, video, or other forms of media content items to the media-playback device 102 based on a heart rate acquired by the heart rate-acquiring device 160 of the media-playback device 102. In accordance with an embodiment, a user U can direct the input 172 to the user interface 164 to issue requests, for example, to play a selected location-based playlist on the media-playback device 102 or to tag a media content item with location data.

Figure 3:
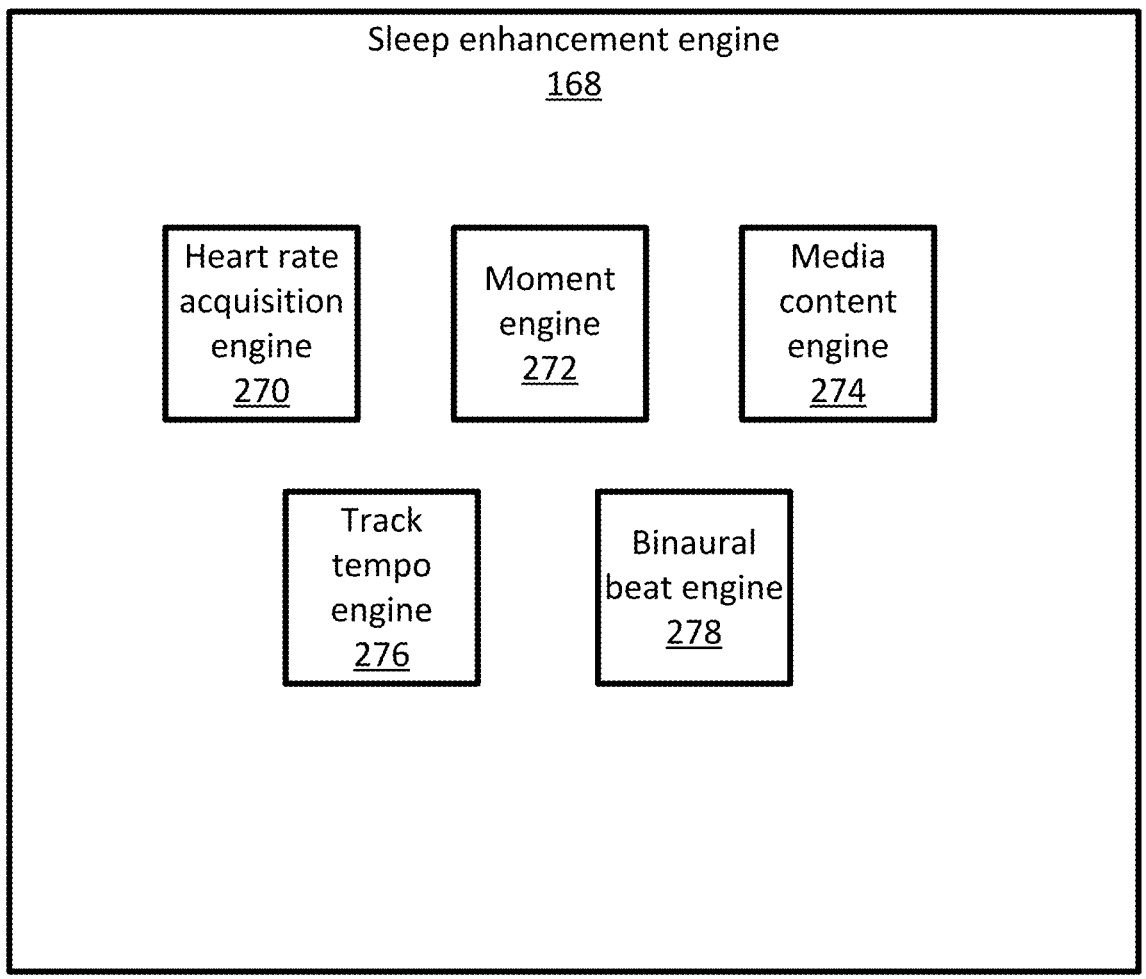
FIG. 3 illustrates a block diagram of an embodiment of the example rest enhancement engine shown in FIG. 2.

FIG. 3 is a schematic block diagram of the rest enhancement engine 168. The embodiment shown includes a heart rate acquisition engine 270, a moment engine 272, a media content engine 274, a track tempo engine 276, and a binaural beat engine 278. Other embodiments can include more or fewer components.

The heart rate acquisition engine 270 operates to acquire a user's U heart rate. Example methods performed by some embodiments of the heart rate acquisition engine 270 are illustrated and described with reference to at least FIG. 4.

The moment engine 272 operates to receive a user's U selection of a moment and determine one or more tracks corresponding to the selected moment. Example methods performed by some embodiments of the moment engine 272 are illustrated and described with reference to at least FIG. 4.

The media content engine 274 operates to select media for playback during rest enhancement. Example methods performed by some embodiments of media content engine 274 are illustrated and described with reference to at least FIG. 4.

The track tempo engine 276 operates to monitor and adjust the tempo of a track playing during rest enhancement. In embodiments, track tempo engine changes the tempo by transitioning between tracks having different tempos. Example methods performed by some embodiments of track tempo engine 276 are illustrated and described with reference to at least FIG. 4.

The binaural beat engine 278 operates to control any binaural beats played by media-playback device 102. Example methods performed by some embodiments of binaural beat engine 278 are illustrated and described with reference to at least FIG. 4.

Figure 4:
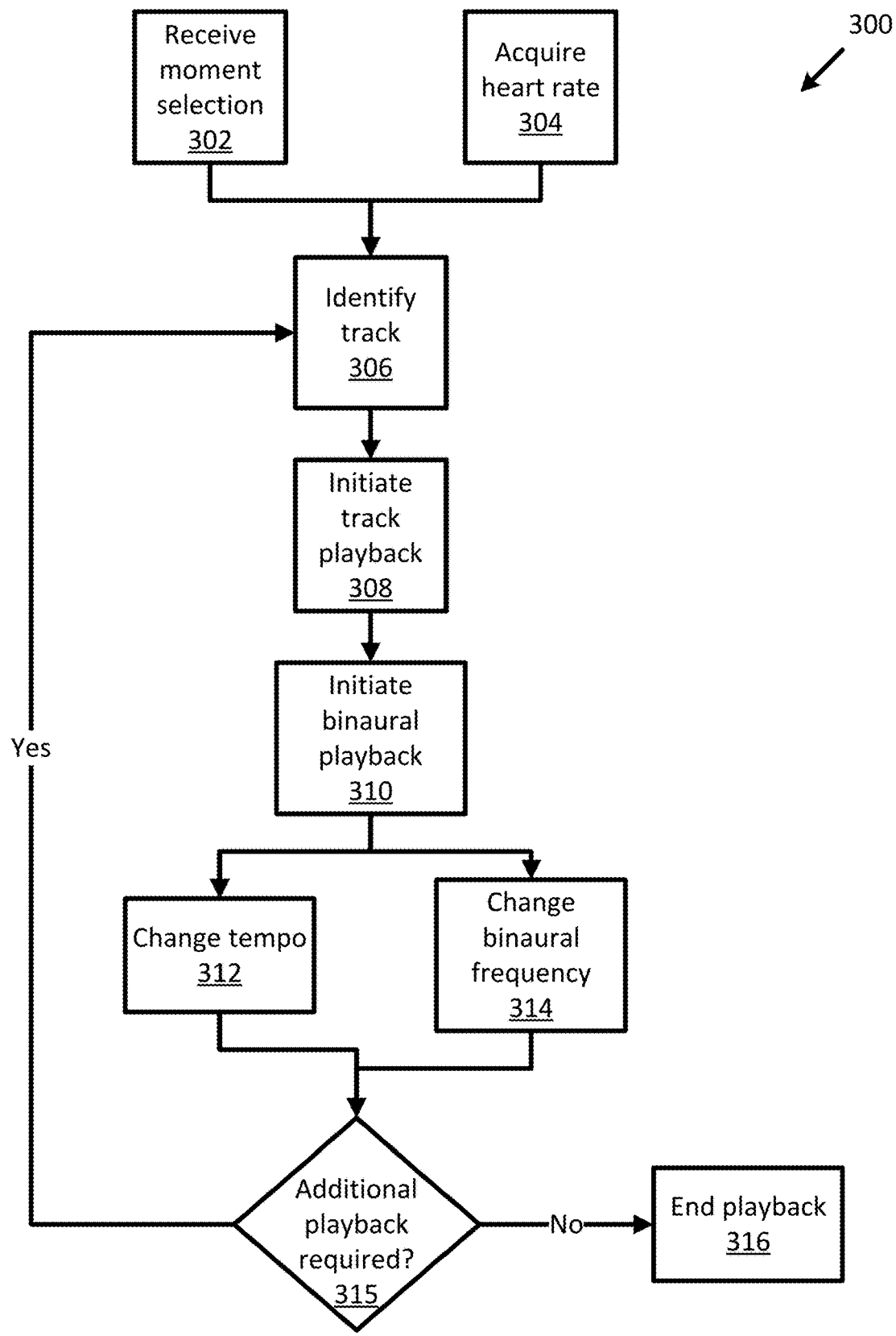
FIG. 4 illustrates a block flow diagram of an embodiment of an example method for rest enhancement.

FIG. 4 is a flow chart illustrating an example method 300 for rest enhancement. As used herein, rest enhancement includes non-sleep activities, such as relaxation, meditation, or an activity such as receiving a massage. The example method 300 includes receiving a moment selection (operation 302), acquiring a heart rate (operation 304), identifying a track (operation 306), initiating track playback (operation 308), initiating binaural playback (operation 310), changing tempo (operation 312), changing binaural frequency (operation 314), determining whether additional playback is required (operation 315), and ending playback (operation 316). Other embodiments can include more or fewer operations.

The example method 300 begins by receiving a moment selection (operation 302). Other embodiments do not include moment selection (operation 302). During operation 302, the media-playback device 102 receives a user's selection of a moment from a collection of moments. For example, moments can include bedtime, power nap, long nap, airplane, kids, commuting, meditation, massage, and prayer.

Various parameters are associated with each moment, such as music type, track playback duration, and additional white noise. For example, white noise can be added to the track playback when the moment received is likely to be associated with extraneous, ambient noise, such as when on an airplane or commuting. Also, as an example, tracks with particular musical instruments can be selected depending upon the moment received.

In some embodiments, the media-playback device 102 presents, and receives a selection of, a content theme, such as nature, symphony, electronic, ambient, atmospheric, white noise, ocean, etc. This selection further defines the types of tracks to play.

In embodiments, some moments include a wake-up component. For example, the commuting moment prompts the user to enter the time until wake up. A user commuting on public transportation, such as a bus, subway, light rail, etc., can be woken up prior to their stop after a period of time has elapsed.

In embodiments, a moment is identified in operation 302 based on contextual information. For example, when a user initiates a sleep function on the mobile device, global positioning satellite (GPS) data may indicate that the user is on a known public transportation route, such as a light rail line, and is moving. Additionally, the time of day might be during normal commuting hours. In that instance, a commuting moment is inferred from the context and offered to the user. As another example, the GPS data may indicate that the user is near his or her home, the device is not moving, and the time is near a normal bedtime. In that instance, a bedtime moment is inferred from the context and offered to the user. Other data can be used to infer context and identify moments.

Example method 300 can also begin by acquiring a heart rate (operation 304). As discussed above with reference to FIG. 2, the media-playback device 102 acquires the heart rate from an external or internal heart rate-acquiring device. Additionally, the user's heart rate can be acquired by the user manually entering their heart rate. If, after acquiring the user's heart rate (operation 304), a moment has not been received, the system 100 can prompt the user to select a moment.

Based on the received moment selection (operation 302) and the acquired heart rate (operation 304), a track is next identified (operation 306). During operation 306, one or more possible tracks are selected from available tracks and filtered according to heart rate and moment tags.

For example, a heart rate of 65 beats per minute (bpm) is received during operation 304 and a selection of a "bedtime" moment is received during operation 302. Based on the heart rate, all tracks not within +/−10% of 65 bpm are filtered out (i.e., those below about 58 bpm and those above about 72 bpm). Additionally, the tracks can be filtered by eliminating any track without a "bedtime" tag, where the tracks stored on media-delivery system 104 have one or more tags.

In embodiments where additional selection criteria are received, those criteria, such as a time duration of the track, can also be used to select applicable tracks.

After qualifying tracks are identified (operation 306), track playback is initiated (operation 308). The track played is a track with a tempo matching the heart rate acquired in operation 304. In embodiments, the system can slow down playback of a track that has a slightly higher tempo than the user's heart rate. For example, if the user's heart rate is 65 bpm, a track with a tempo of 70 bpm may be selected but slowed down to be played at 65 bpm. Then the tempo of the track is slowed until playback ends (operation 316).

Alternatively, a track is played that has a tempo slower than the user's heart rate. For example, if the user's heart rate is 65 bpm, a track with a tempo of 60 bpm is played (operation 308). That track can be played at that tempo until playback ends (operation 316) or the track tempo can be further slowed down during playback.

In some embodiments, a track from the filtered list of tracks is randomly selected for playback. Alternatively, all tracks meeting the filter criteria are presented to the user and the user selects a particular track for playback.

During track playback (operation 308), the audio of the track is played for the user through one or more speakers in the media-playback device, or the audio is played through one or more speakers in communication with the media-playback device.

In some embodiments, binaural beat playback (operation 310) is initiated concurrent with, or shortly after, track playback initiation (operation 308). Generally, binaural beats are perceived sounds created by playback of two different tones at different frequencies. Generally, "binaural" refers to the difference in frequencies of each tone. For example, if a tone with a frequency of 300 Hz was played in one ear, and a second tone with a frequency of 310 Hz was played in the other ear, then the binaural beat would have a frequency of 10 Hz.

At the beginning of binaural beat playback (operation 310), alpha binaural beats are played, which are typically close to the user's starting dominant frequency. Generally, alpha binaural beats have a frequency of about 7 Hz to about 13 Hz. In embodiments, a binaural beat of 12 Hz is initially played back during operation 310. In embodiments, the binaural beat is mixed with the track audio. In other embodiments, the track already includes the binaural beat.

In some embodiments, during track playback, the tempo is changed (operation 312) and the binaural frequency is changed (operation 314). In embodiments, these changes occur at the same relative rate.

In some embodiments, only the binaural frequency is changed (operation 314), i.e., the tempo remains constant. That is, at least some embodiments of example method 300 do not include changing tempo operation 312. In those embodiments, the track playback begins at a tempo that is less than the acquired heart rate by about 4%; about 5%; about 6%; about 7%; about 8%; about 9%; about 10%; about 11%; or about 12%. For example, if a heart rate of 60 bpm is acquired in operation 304, then the track is played at 55 bpm, or about 8% less than the acquired heart rate.

Operation 312 includes decreasing the tempo of the track by about 4%; about 5%; about 6%; about 7%; about 8%; about 9%; about 10%; about 11%; or about 12%. These decreases in tempo can be achieved in multiple ways, such as mechanically slowing a track, playing multiple tracks with different tempos, playing different versions of the same track recorded at different tempos, or playing a track whose tempo decreases. As an example, if heart rate acquired in operation 304 is 65 bpm, and a track with a tempo of 65 bpm is played in operation 308, then during playback the tempo is slowed to 60 bpm.

In some embodiments, more than one track is played before ending playback (operation 316). There, the track tempo can be decreased with each new track played, such as first playing a track with a tempo of 65 bpm, then playing a track with a tempo of 60 bpm, and then playing a track with a tempo of 55 bpm.

In some embodiments, the track selected for playback slowly has a decreasing tempo, that is, the tempo at the beginning of the track is faster than the tempo at the end of the track.

In some embodiments, a given track is recorded at a plurality of different tempos. For example, a track with a particular melody is recorded at each of 45 bpm, 50 bpm, 55 bpm, 60 bpm, 65 bpm, 70 bpm, and 75 bpm. Then, during playback, the tempo of the track is changed by cross-fading between tracks. For example, a track with a tempo of 65 bpm is initially played and slowed to 62 bpm. Then that track is cross-faded with a second track having a tempo of 60 bpm that has been sped up to 62 bpm. After cross-fading, the second track is slowed down to 60 bpm or slower. An example of changing the tempo is shown and described in detail with reference to FIG. 12, below.

As the track is played (operation 308), the binaural frequency is changed (operation 314). As mentioned above, an alpha binaural beat is played at the beginning of track playback. Then, during track playback, the binaural beat is changed (operation 314) to be theta binaural beats, that is, binaural beats in the 4 Hz to 7 Hz range, for example.

In some embodiments, the track selected for playback in operation 306 is not long enough to play the entire duration of restful time. After the track ends, or is close to ending, operation 315 determines whether additional playback is required. For example, if the moment has a 20-minute playback time period, and the track ends after 8 minutes, then 12 more minutes of track playback are needed. If additional track playback is needed, then the example method 300 may return to operation 306 to select another track. The example method 300 continues this loop until there has been enough track playback for the given moment. In some embodiments, the track is extended by finding loop-able sections and seamlessly jumping back in time until the entire track plays for the requested duration. If no additional playback is required, then playback ends (operation 316).

Figure 5:
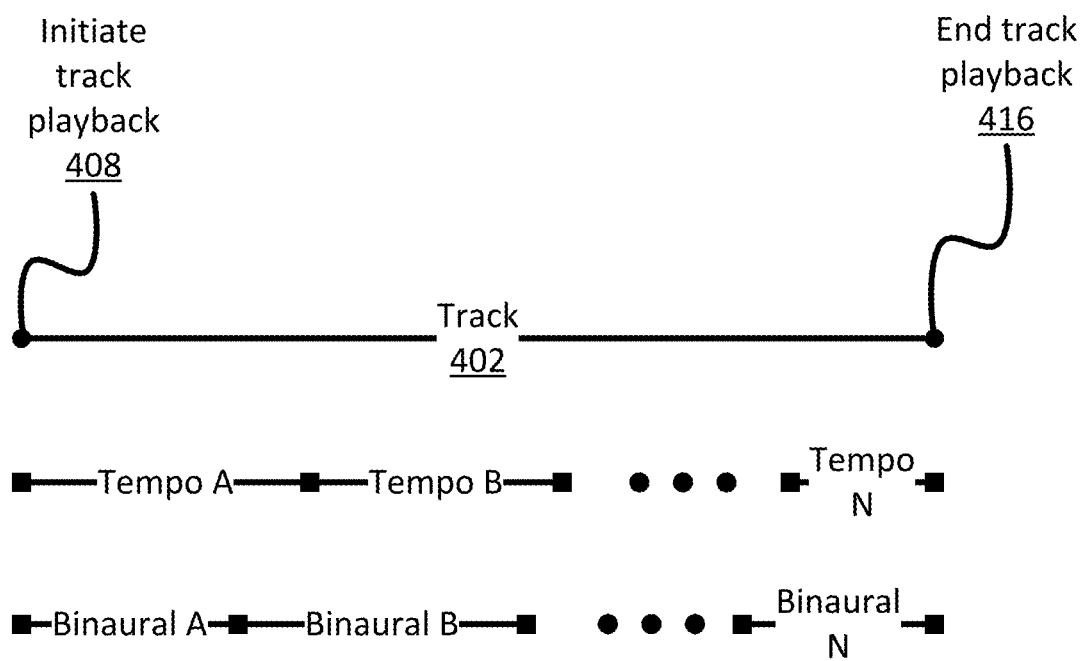
FIG. 5 illustrates a schematic diagram of an embodiment of a first example track.

FIG. 5 is a schematic illustration of an example track 402 during music playback. The beginning of track 402 corresponds to the initiation of track playback (operation 308). The end of track 402 corresponds to end of playback (operation 316). That is, in this example, only a single track 402 is played during the entire restful period.

Track 402 has a tempo A at the beginning of the track. As discussed with respect to example method 300, in one example the tempo A corresponds to a user's heart rate. During track playback, the tempo of track 402 is changed to have N tempos, where N is greater than or equal to 1. As an example, tempo A is 72 bpm, tempo B is 68 bpm, and tempo N is 64 bpm.

As shown in FIG. 5, the track can be played at a first tempo, tempo A, for a given period of time. Then, the track tempo is adjusted to a new tempo, tempo B, which plays for a second given period of time. In some embodiments, as discussed above, a given track 402 may have multiple recordings at different tempos. In those embodiments, the track tempo is altered by cross-fading to a different version of the same track recorded at a different tempo.

In other embodiments, track tempo A is changed throughout playback at a constant rate. For example, the track tempo is reduced by 0.4 bpm every minute. In embodiments where the track playback duration is 20 minutes, then, the track tempo would be 8 bpm slower at end track playback (operation 316).

Also shown in FIG. 5 are the binaural beats, binaural A, binaural B, up to binaural N, played during track 402. As shown, a plurality of binaural beats are played during track playback and the beats are changed at different times than the tempo is changed. In some embodiments, the initial binaural beat A is decreased at a constant rate, for example, at 0.3 Hz per minute. In other embodiments, the binaural beat frequency is altered by a given amount every time period, such as a 1 Hz decrease every 3 minutes.

Figure 6:
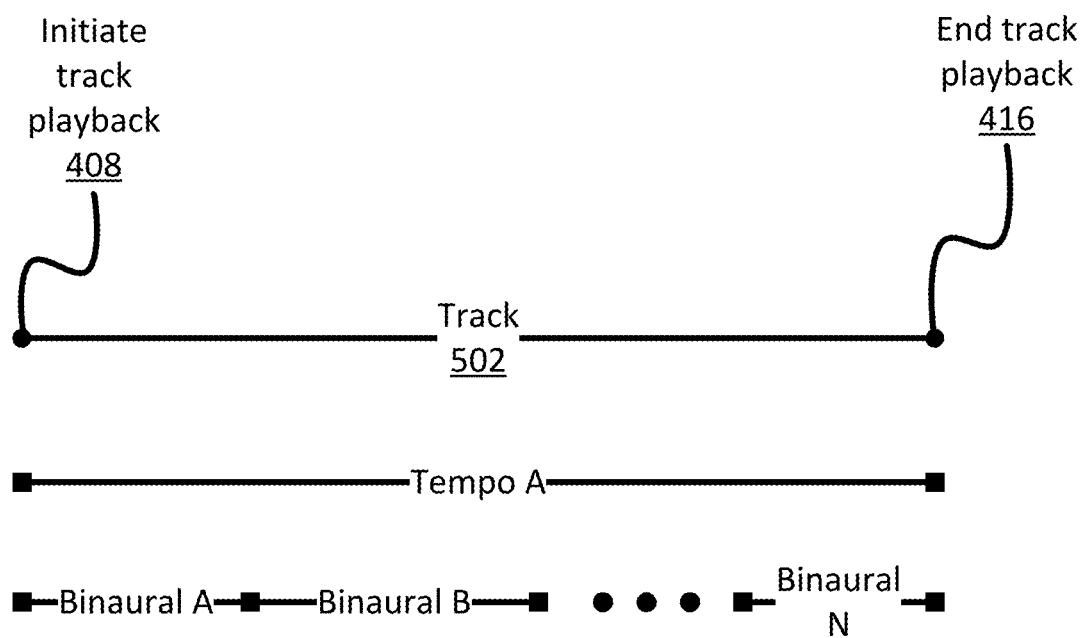
FIG. 6 illustrates a schematic diagram of an embodiment of a second example track.

FIG. 6 illustrates an embodiment of an example track 502 during music playback. In the embodiment shown, a single track is played from initiating track playback (operation 308) until ending track playback (operation 316).

As shown, track 502 is played at the same tempo, Tempo A, throughout playback. This tempo corresponds to the acquired heart rate of the user. For example, if the acquired user heart rate is 75 bpm, then tempo A is lower than that heart rate, for example, 70 bpm. In other embodiments, multiple tracks can be played at the same tempo, tempo A.

Also shown in FIG. 6 is the binaural beats, binaural A, binaural B, up to binaural N, played during track 502. As shown, a plurality of binaural beats are played during track playback. In some embodiments, the beats are changed at different times than the tempo is changed. In some embodiments, the initial binaural beat A is decreased at a constant rate, for example, at 0.3 Hz per minute. In other embodiments, the binaural beat frequency is altered by a given amount every time period, such as a 1 Hz decrease every 3 minutes.

FIGS. 7, 8, 10, and 11 illustrate an example series 702 of user interface screens shown on a mobile device 704 during example method 300, illustrated and described with reference to FIG. 3. The mobile device 704 is, for example, a smart mobile phone, a tablet computer, or a smart watch.

Figure 7:
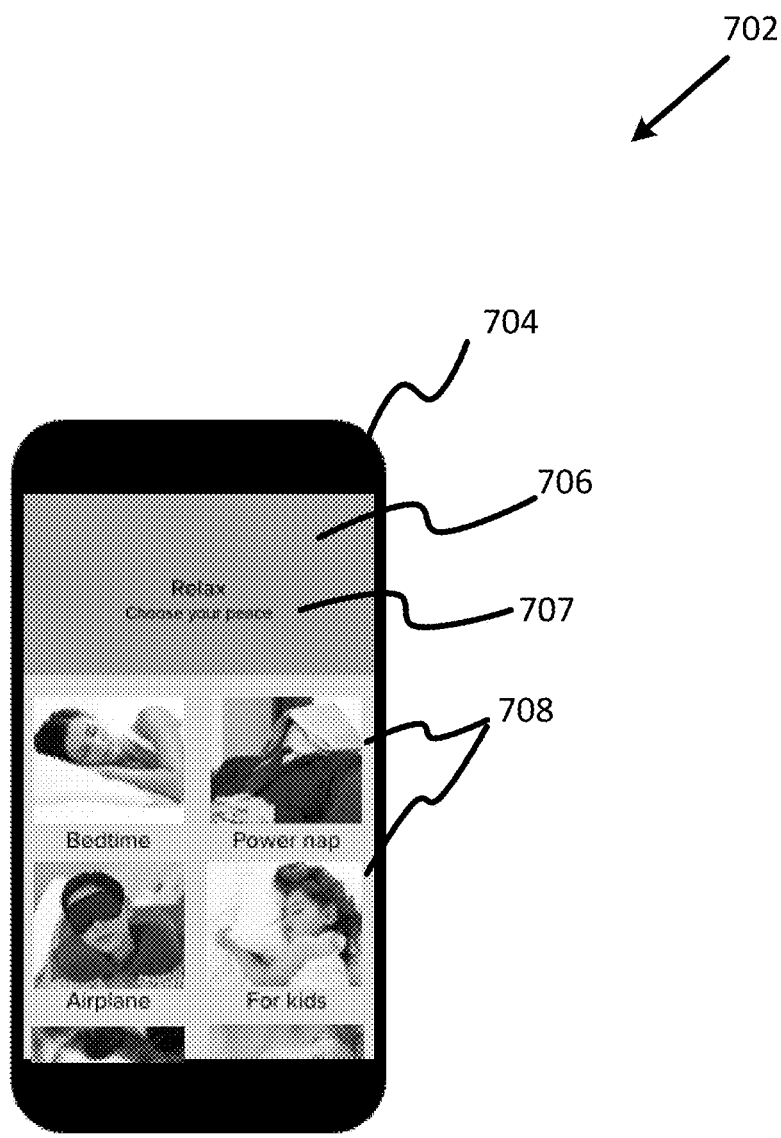
FIG. 7 illustrates a first user interface of an embodiment of an example screen shown on a mobile device.

FIG. 7 illustrates an embodiment of a moment selection screen 706. The moment selection screen 706 includes instructions 707 and moments 708. Example moments 708 shown include bedtime, power nap, airplane, and for kids. The user can scroll down to reveal additional moments 708, such as those listed above with reference to FIGS. 1-6.

Figure 8:
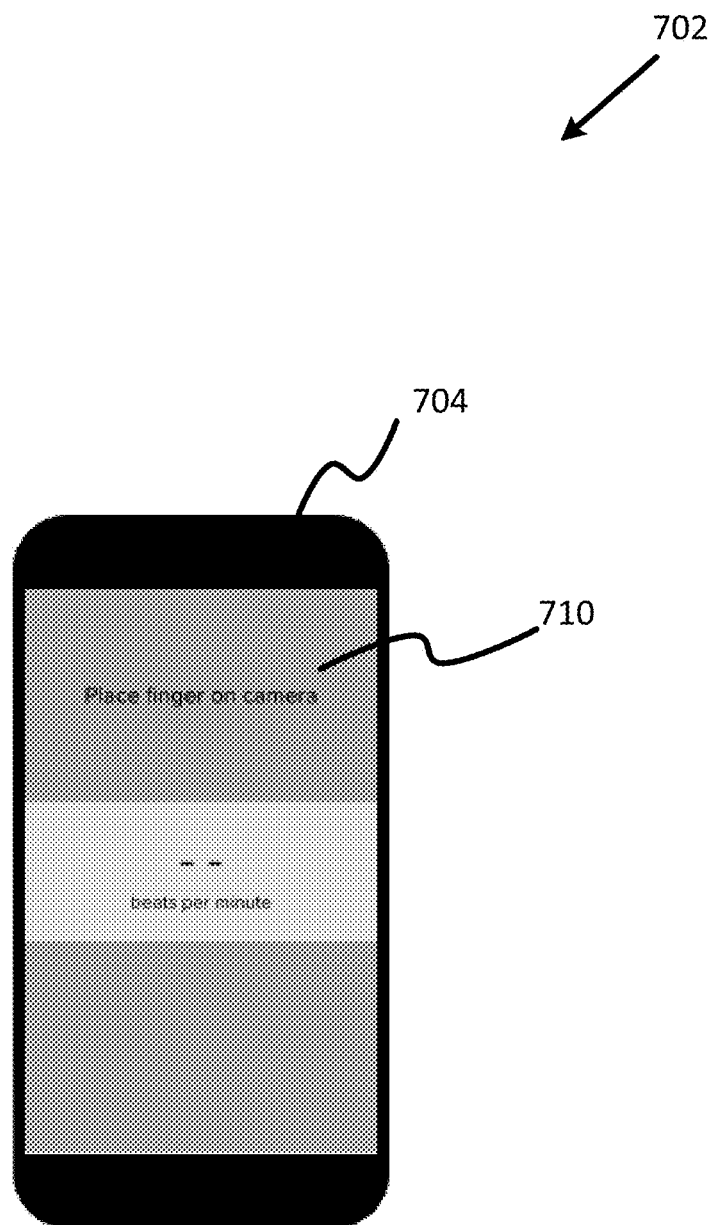
FIG. 8 illustrates a second user interface of the embodiment of an example screen shown on a mobile device of FIG. 7.

FIG. 8 indicates an embodiment of a heart rate acquisition screen 710. As discussed above, mobile device 704 can acquire the user's heart rate using internal hardware and/or from external devices. In the embodiment shown, heart rate acquisition screen 710 instructs the user to place his or her finger on the mobile device's camera.

Figure 9B:
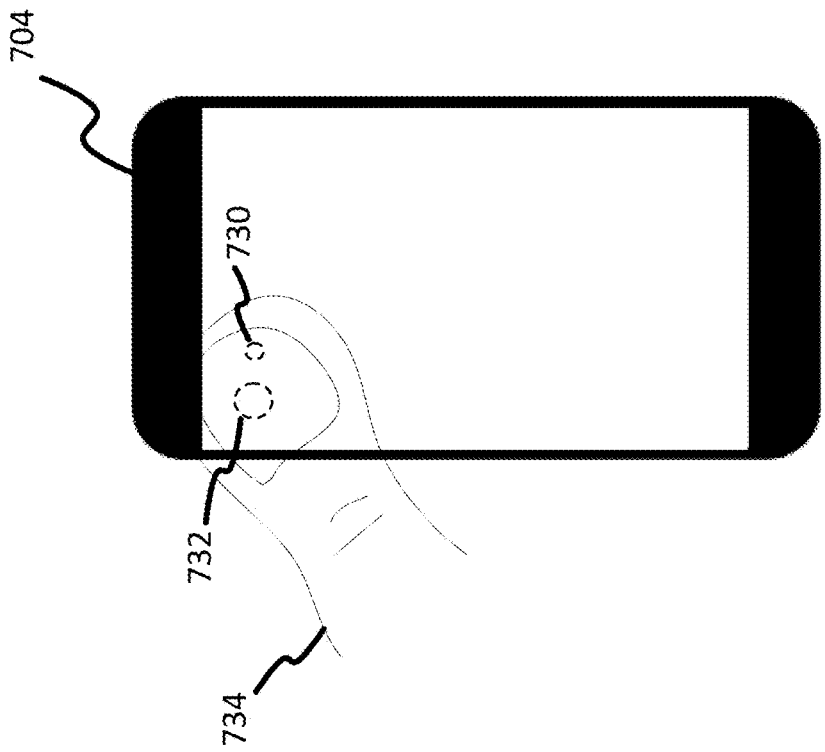
FIG. 9B illustrates a user's finger positioned near the rear portion of the example media device shown in FIG. 9A.
Figure 9A:
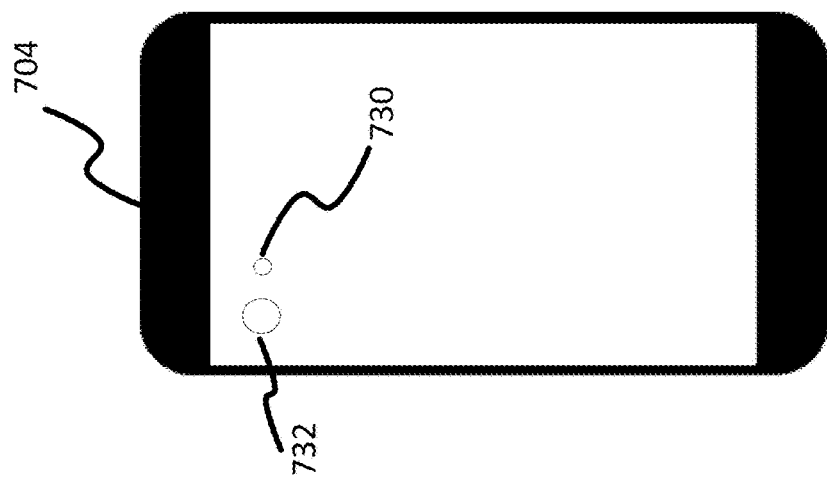
FIG. 9A illustrates a rear portion of an example media device.

FIGS. 9A and 9B illustrate an embodiment of the example mobile device 704 acquiring a heart rate. FIG. 9A illustrates a surface of example mobile device 704 that includes a camera 732 and light source 730. Camera 732 and light source 730 are positioned relatively adjacent to each other so they can both be covered by a single finger at the same time. Also, camera 732 and light source 730 are in communication with the processing device and memory device of the mobile device 704.

FIG. 9B illustrates a user's finger 734 positioned over the camera 732 and light source 730. During heart rate acquisition, the light source 730 generates light and illuminates the user's finger. The camera 732 receives the light from the user's illuminated finger. The mobile device 704 analyzes the images to determine a heart rate of the user by tracking color changes in the user's illuminated finger.

The heart rate acquisition screen 710 can additionally include instructions for the user to hold his or her finger 734 over the camera 732 and light source 730 until a heart rate is acquired. Upon heart rate acquisition or determination, the mobile device 704 can provide visual, audio, or haptic notification that the user can remove his or her finger 734.

Figure 10:
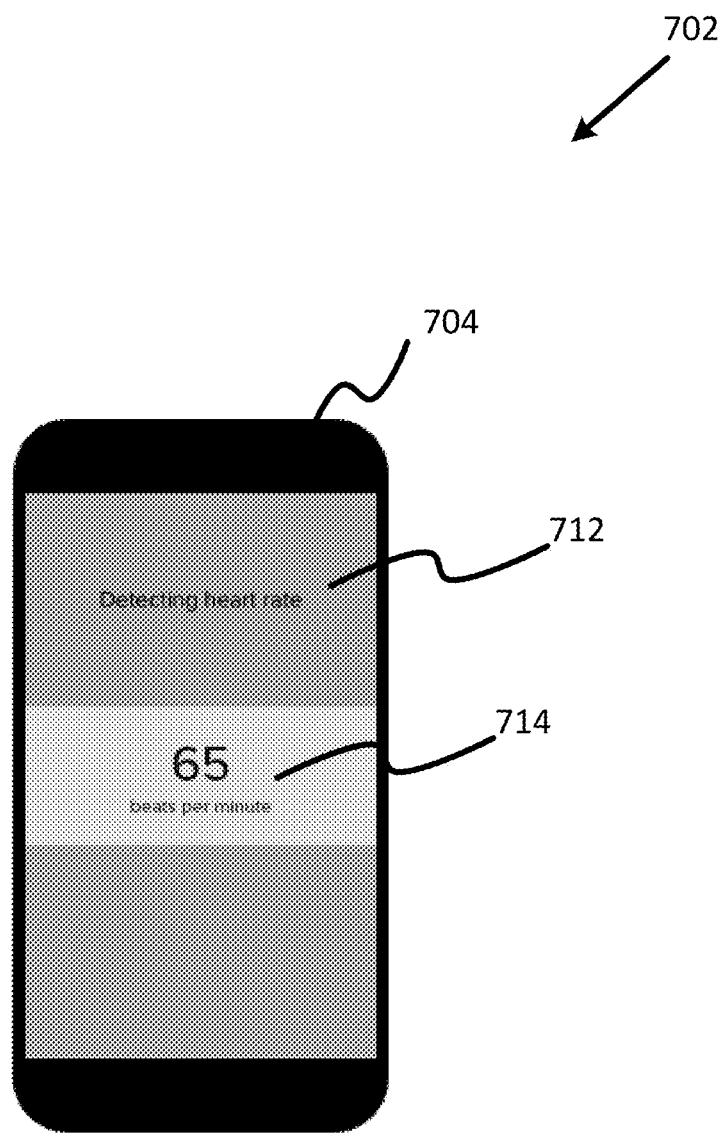
FIG. 10 illustrates a third user interface of the embodiment of an example screen shown on a mobile device of FIG. 7.

FIG. 10 illustrates an embodiment of a heart rate display screen 712. The heart rate display screen 712 indicates the acquired user heart rate 714, shown in beats per minute.

Figure 11:
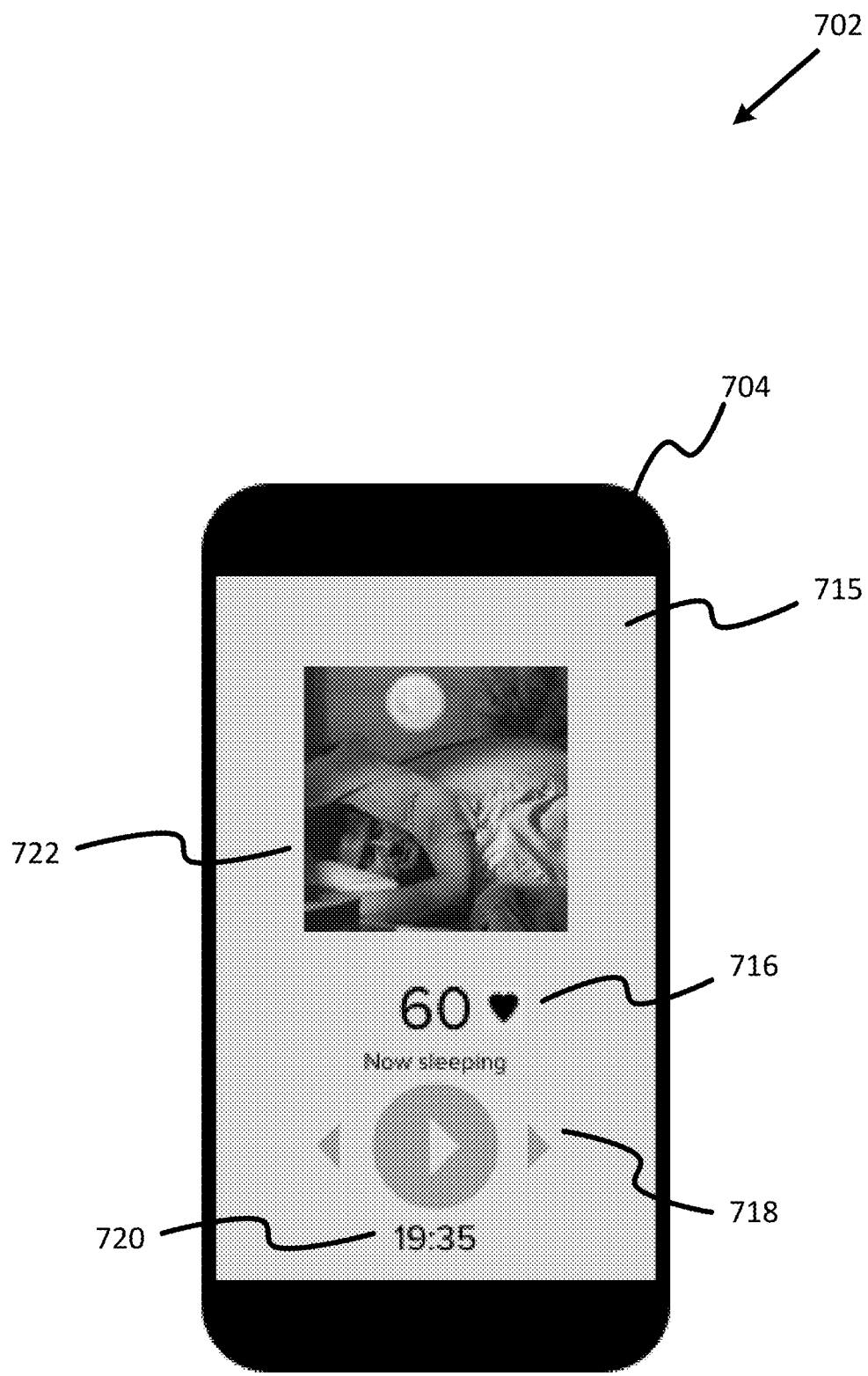
FIG. 11 illustrates a fourth user interface of the embodiment of an example screen shown on a mobile device of FIG. 7.

FIG. 11 illustrates an embodiment of a playback screen 715. The playback screen 715 includes a tempo display 716, a track navigation 718 section, a playback time indicator 720, and a moment indicator 722. Playback screen 715 is displayed on mobile device 704 after acquiring a heart rate and determining a moment. Other embodiments can include more or fewer components, such as options for changing the moment or tempo.

The tempo display 716 shows the tempo of the current track. The track navigation 718 section includes user-selectable controls that enable the user to start, stop, or pause the track, to select a different track, to return to the start of the track, or to return to the previous track.

Playback time indicator 720 shows the time remaining until playback ends. Alternatively, playback time indicator 720 shows the time elapsed since playback began. Moment indicator 722 displays a representation of the moment selected by the user.

Figure 12:
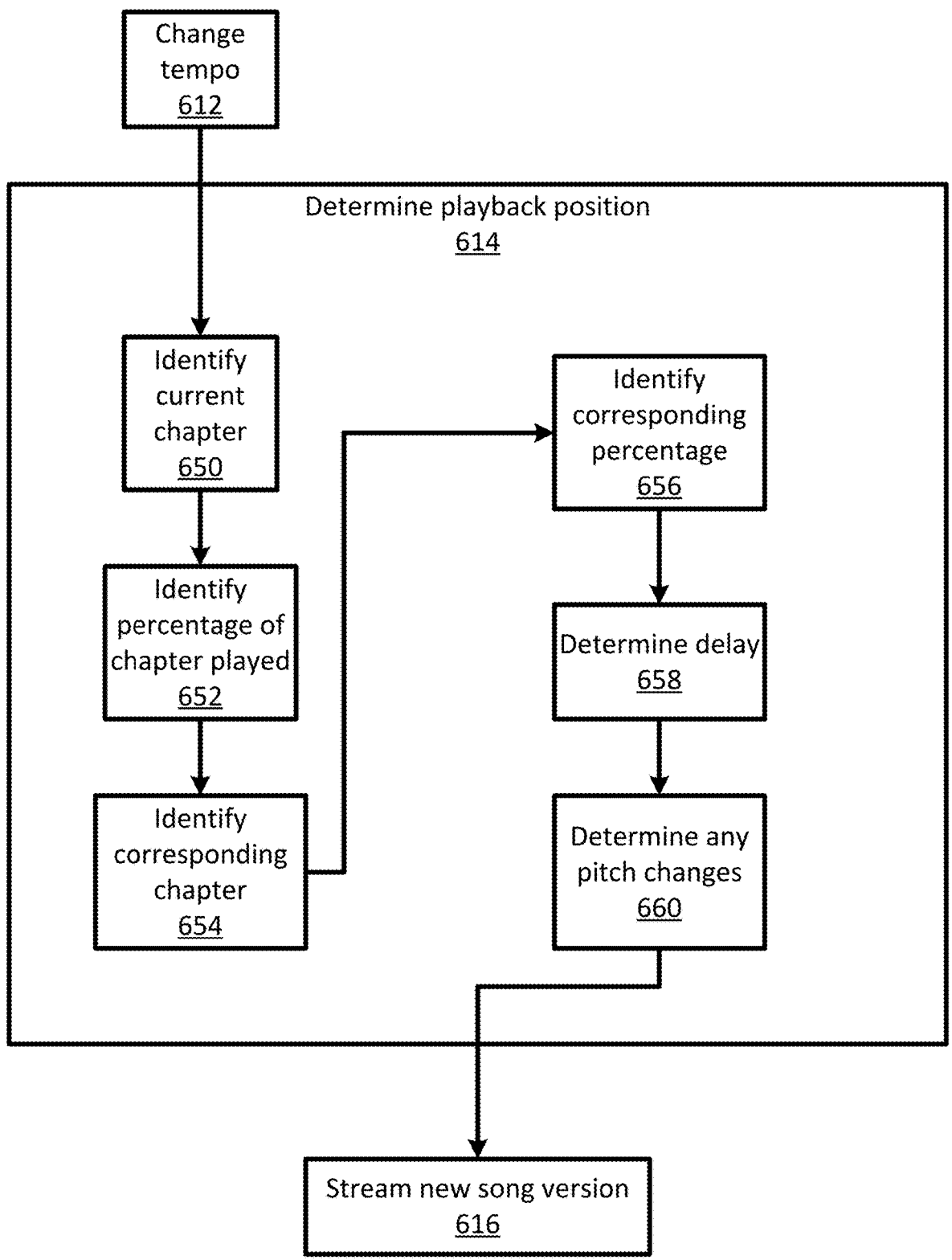
FIG. 12 illustrates a block flow diagram of an example method for determining playback position of a second track.

FIG. 12 illustrates an example method 614 of determining a playback position. In this example, the method 614 includes operations 650, 652, 654, 656, 658, and 660. Also shown is a change tempo input (operation 612) and a stream new song version operation 616. In some embodiments, the change tempo input (operation 612) corresponds to the change tempo operation 312 shown and discussed with reference to FIG. 3. Other embodiments can include more or fewer operations.

The tracks played during the example method 614 shown in FIG. 12 have more than one version recorded at different tempos. Each track version can include one or more chapters and the chapters are consistent across track versions for a particular track.

After receiving a change tempo input (operation 612), a chapter of the currently-playing track version is identified (operation 650). Operation 650 can include retrieving metadata, for example, chapters, duration of the track version, duration of the chapters, etc., about the track versions. Additionally, operation 650 can include retrieving metadata that includes the relationship between related track versions. For example, a playback position of the currently-playing track version is 14:30, or fourteen minutes thirty seconds, and is in chapter 4.

Next, the percentage of the chapter played is identified (operation 652). Using the example above, the playback position of the currently-playing track version is 14:30 and is in chapter four, which started at 12:00 and ends at 16:30 in the track version. That is, the current chapter is 4:30 in length and 2:30 have played, thus the percentage of the chapter played is about 56%. In some embodiments where the track versions are not divided into chapters, the percentage of the track version played can be determined after operation 610, for example, rather than the percentage of the chapter (operation 652).

After determining the current chapter and percentage of the chapter played, a corresponding chapter (operation 654) and corresponding percentage of the chapter (operation 656) are determined for the next track version. Using the example discussed with reference to operation 650, the currently-playing track version is in chapter four. Thus, the corresponding chapter for beginning playback of the next track version is chapter four.

Next, about 56% of chapter 4 has been played in the currently-playing track version. Thus, playback of the next track version will begin at about 56% of chapter 4 of the next track version. If the next track version's chapter 4 starts at 11:00 and ends at 15:00, which is four minutes in length, then playback will begin about two minutes and fourteen seconds into the fourth chapter, or at about 13:14 of the entire track version. This starting position might be modified depending on any delay or cross-fading determination in operation 658.

Any delays to accommodate transitioning to the next track version are determined in operation 658. For example, any cross-fading times can be accounted for during operation 658.

Also, the beats of the currently-playing track version and the next track version can be aligned. As an example, an alignment includes any adjustments to make the first beat of each measure in the currently-playing track version align with the first beat of each measure in the next track version. This alignment can include temporarily adjusting the tempo of the currently-playing track version, the tempo of the next track version, or both, such that they match when the next track version is streamed.

After determining the playback location of the next track version, any pitch changes are next determined (operation 660). For example, when transitioning from a currently-playing track version at a tempo of 65 bpm to a next track version at a tempo of 55 bpm, the pitch of the next track version is lowered during the cross-fading. This pitch change can potentially correct any changes in pitch when the tempo of one or both of the track versions is adjusted. After or during cross-fading, the pitch is increased again, for example, over about 0.5 second, about 1 second, about 2 seconds, about 3 seconds, about 4 seconds, or about 5 seconds until it is back at the original pitch. Alternatively, or in combination, the pitch of the currently-playing track version is increased during cross-fading.

In some embodiments, pitch is managed, for example, by decreasing tempo without decreasing pitch, selecting only songs that match in pitch, or slowly adapting the pitch over a long period of time to detune in a manner unnoticeable to the listener. Each of these transformations can be continuous, as opposed to steps, over periods of time, including tempo and pitch. Further, crossfading can also include beat-matching.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method for selecting and playing a song with a mobile device, the method comprising:
receiving a request from a user to play a song;
receiving a context selection for a context for playback;
detecting a user heart rate using a sensor and a light source of the mobile device, while the sensor and the light source are directed toward a part of the user's body;
selecting a first song with a first tempo, wherein the first tempo is based on the user heart rate and the context selection;
mixing a binaural beat with the first song;
initiating playback of the first song, with the first tempo, and the binaural beat on the mobile device; and
over a predetermined amount of time, reducing a frequency of the binaural beat.

2. The method of claim 1, wherein the first song with a first tempo is a first version of the first song, and further comprising:
receiving a change tempo input; and
initiating playback of a second version of the first song, wherein the second version of the first song has a second tempo.

3. The method of claim 2, further comprising:
while initiating playback of the second version of the first song, initiating cross-fading between the first version of the first song and the second version of the first song; and
after initiating cross-fading, stopping playback of the first version of the first song.

4. The method of claim 3, wherein the first tempo is faster than the second tempo.

5. The method of claim 3, wherein a plurality of versions of the first song are stored on the mobile device, each version of the first song having a different tempo.

6. The method of claim 2, wherein receiving a change tempo input includes reducing the tempo by a predetermined rate over time based on a moment selection.

7. The method of claim 6, wherein the tempo is reduced by 0.4 beats per minute every minute.

8. The method of claim 1, wherein the context is a moment, and wherein receiving the context selection includes one of receiving a moment section selection from a user input or receiving a moment selection based on contextual information.

9. The method of claim 8, wherein the contextual information is global positioning system data.

10. The method of claim 8, wherein the moment selection is one of bedtime, power nap, long nap, airplane, kids, commuting, meditation, massage, or prayer.

11. The method of claim 1, wherein the first tempo is further based on the binaural beat.

12. The method of claim 1, wherein the sensor is a camera.

13. The method of claim 1, further comprising:
after detecting the user heart rate, indicating to the user that the user heart rate was detected.

14. A system for selecting and playing a song, comprising:
a processing device;
a database storing a plurality of songs, wherein the database is in communication with the processing device;
a speaker in communication with the processing device;
a heart rate-acquiring device in communication with the processing device; and
a computer readable storage device storing data instructions which, when executed by the processing device, cause the system to:
receive a request from a user to play a song for a moment;
receive a moment selection;
acquire a user heart rate;
select a first song with a first tempo, wherein the first tempo is based on the user heart rate and the moment selection;
initiate playback of the first song with the first tempo on the mobile device;
initiate playback of a second version of the first song, wherein the second version of the first song has a second tempo and the second tempo is slower than the first tempo;
while initiating the playback of the second version of the first song, initiate cross-fading between the first version of the first song and the second version of the first song; and
after initiating cross fading, stop the playback of the first version of the first song.

15. The system of claim 14, wherein the heart rate-acquiring device is a mobile device having a camera and a light source, wherein the camera and the light source are positioned adjacent to each other so they can both be covered by a single finger at the same time.

16. The system of claim 14, wherein the heart rate-acquiring device is one of a watch, wrist band, or chest strap.

17. The system of claim 14, wherein the speaker communicates with the processing device wirelessly.

18. The system of claim 14, wherein the instructions further cause the system to:
initially increase the second tempo of the second song to a third temp that matches the first tempo of first song;
align beats of the second song with beats of the first song;
after aligning the beats, initiate playback of the second song in conjunction with the first song; and
after stopping the playback of the first version of the first song, slow the playback to match the second tempo.

19. A non-transitory computer readable medium having instructions stored therein that, when executed by a processor within a mobile device, cause the mobile device to:
receive a request from a user to play a song for a moment;
receive a moment selection;
instruct a user to place a finger over a camera and a light source on the mobile device;
illuminate the finger of the user;
while the finger of the user is illuminated, acquire a user heart rate with the mobile device;
after acquiring the user heart rate, indicate to the user to remove the finger from the camera and the light source;
select a first song with a first tempo, wherein the first tempo is based on the user heart rate and the moment selection;
initiate playback of the first song with the first tempo on the mobile device;
receive a change tempo input;
initiate playback of a second version of the first song, wherein the second version of the first song has a second tempo and the second tempo is slower than the first tempo;

while initiating playback of the second version of the first song, initiate cross-fading between the first version of the first song and the second version of the first song; and after initiating cross-fading, stop playback of the first version of the first song.

\* \* \* \* \*